(12) United States Patent
Sorkey et al.

(10) Patent No.: US 12,087,412 B1
(45) Date of Patent: Sep. 10, 2024

(54) ELECTRONIC IDENTIFICATION OF HEALTHCARE PATIENTS

(71) Applicant: Zeus Data Solutions, Inc., Shreveport, LA (US)

(72) Inventors: Alan J. Sorkey, Shreveport, LA (US); Steven Allen Conrad, Shreveport, LA (US)

(73) Assignee: Zeus Data Solutions, Inc., Shreveport, LA (US)

( * ) Notice: Subject to any disclaimer, the term of this patent is extended or adjusted under 35 U.S.C. 154(b) by 374 days.

(21) Appl. No.: 17/122,589

(22) Filed: Dec. 15, 2020

Related U.S. Application Data

(63) Continuation of application No. 13/093,519, filed on Apr. 25, 2011, now abandoned.

(51) Int. Cl.
*G06K 9/00* (2022.01)
*G05B 19/00* (2006.01)
*G16H 10/60* (2018.01)
*G06V 40/16* (2022.01)

(52) U.S. Cl.
CPC .......... *G16H 10/60* (2018.01); *G06V 40/161* (2022.01)

(58) Field of Classification Search
CPC .............................. G16H 10/60; G06V 40/161
See application file for complete search history.

(56) References Cited

U.S. PATENT DOCUMENTS

| | | | |
|---|---|---|---|
| 4,821,118 A | 4/1989 | Lafreniere | |
| 5,991,429 A | 11/1999 | Coffin | |
| 6,681,032 B2 | 1/2004 | Bortolussi | |
| 7,128,258 B1 | 10/2006 | Harper | |
| 7,152,785 B2 | 12/2006 | Metz | |
| 7,593,549 B2 | 9/2009 | Reiner | |
| 7,602,947 B1 | 10/2009 | Lemelson | |
| 7,643,671 B2 | 1/2010 | Dong | |
| 7,684,595 B2 | 3/2010 | Kamgar-Parsi | |
| 2001/0041991 A1 | 11/2001 | Segal | |
| 2004/0049687 A1 | 3/2004 | Orsini | |
| 2006/0206942 A1 | 9/2006 | Sweet | |
| 2007/0172155 A1 | 7/2007 | Guckenberger | |
| 2007/0279187 A1* | 12/2007 | Hekmatpour | G16H 10/60 340/5.82 |
| 2008/0126809 A1 | 5/2008 | Rothschild | |
| 2009/0243833 A1 | 10/2009 | Huang | |
| 2009/0328138 A1 | 12/2009 | Lee | |
| 2010/0333194 A1 | 12/2010 | Ricordi | |
| 2011/0031071 A1 | 2/2011 | Takeuchi | |
| 2011/0153341 A1 | 6/2011 | Diaz-Cortes | |

(Continued)

*Primary Examiner* — Maroun P Kanaan
(74) *Attorney, Agent, or Firm* — Fish & Richardson P.C.

(57) ABSTRACT

A computer-implemented method for selectively providing access to medical record information is disclosed. The method includes receiving, at a computer system, one or more digital images of a healthcare patient from a computing device that corresponds to a user account that is authorized to obtain information about patients in a healthcare system; using computerized facial recognition to identify the person as being one or more registered members of the healthcare system and to obtain a member identifier; using the member identifier to obtain electronic medical record information about the person; and providing some or all of the obtained electronic medical record information to the computing device.

13 Claims, 10 Drawing Sheets

(56) References Cited

U.S. PATENT DOCUMENTS

2011/0213210 A1    9/2011  Temby
2012/0313785 A1* 12/2012  Hanson ................ A61B 5/4833
                                                  340/573.1

* cited by examiner

ELECTRONIC IDENTIFICATION OF HEALTHCARE PATIENTS

TECHNICAL FIELD

This document relates to automatic identification of patients in a healthcare setting so as to enable, for example, accelerated and simplified access to patient record information.

BACKGROUND

The formation of and use of electronic medical records (EMRs) is a great goal of many healthcare organizations and of the federal government. EMRs may allow physicians to access information about particular patients immediately and from numerous locations, such as from their homes. Also, when EMRs are available, a patient need not worry about a single physical location at which their "file" is located, since they can go to a variety of facilities and their record will follow them. However, the easy portability and accessibility or medical records also raises concerns about patient privacy, particularly for certain types of information.

Patient interaction with healthcare providers can also be a taxing process. For example, a patient may have to fill out a number of forms when visiting a clinic or hospital, and may have to submit his or her name, address, and other identifying information multiple time. Such information may then need to be transcribed by a staff person so that the patient's visit may be recorded and properly billed. All of this makes the experience unhappy for the patient, and expensive and potentially error-prone for the healthcare provider.

SUMMARY

This document describes systems and techniques that may be used for automated identification of patients in a healthcare setting. Such automated identification can be particularly helpful when the patients cannot communicate, such as when a patient at the scene of an automobile accident is unconscious.

In general, by the techniques described here, one or more digital images of a patient may be captured (including as frames in a digital video), and the images may be compared to data from images of known potential patients, such as images of registered users within a healthcare system. The identified patient's electronic medical record (EMR) information may then be retrieved using the automatic identification. In certain instances, the system for performing the identification may be kept separate from the EMR system so as to maintain patient privacy; for example, the EMR system may send image data to the facial recognition system, which may in turn produce an ID number that can be mapped to particular patients only by the EMR system (so that the facial recognition system cannot obtain such data). Also, the data that represents the images may be run through a one-way function, such as a hash having a sufficiently large target space to be able to resolve image matches accurately, so that the facial recognition system is not able to reconstruct the initial images that it is provided by a more secure system. In this manner, in certain implementations, the facial recognition system can be operated by a third party as a service provided to multiple healthcare providers.

Certain metadata may be acquired with the images to aid in resolving a patient's identity. For example, a person who acquires an image of the patient, such as an emergency medical technician, admissions officer, or the like, can provide information about the patient's race, gender, and approximate height and weight. In addition, the geographic location at which the images were acquired may be captured (e.g., automatically by GPS functionality in a camera or portable computer containing a camera that captures the images). Such information may be used to disambiguate a situation in which multiple pre-acquired images of enrolled patients appear to match the current images of a prospective patient. For example, EMR data for each patient who corresponds to a matching image may be retrieved, and the relevant data (gender, age, race, weight, location of the image acquisition compared to the patient's home address, etc.) may be compared to the EMR data.

Depending on the situation in which the image is submitted, various information about a matching patient may be delivered, such as to the device that submitted the images (e.g., an EMT's slate computer) or to an attached device (e.g., a desktop computer attached to a camera in an admissions area). To determine what information should be provided, for example, an identifier for the healthcare provider who submitted the images may be provided to the system with the images, and the provider may be matched to a class of providers that have a certain level of access to patient information. As one example, an EMT may be provided with limited access, such as being provided with critical data for the patient such as patient blood type and serious allergies. In contrast, a treating physician in an emergency room may be provided with complete EMR data. Also, the EMT could be connected with a physician before the EMT gets the patient to the emergency room, and the physician may increase the level of access that the EMT has to the patient's information if the physician deems such access necessary.

To help ensure that a match was accurate, the person who submitted the images may also be provided with the previously-acquired image of the patient. Such an image may be displayed to the healthcare provider side-by-side with the just-captured image, so that the provider can manually verify that they are looking at the patient information for the right person.

In certain implementations, such features may provide one or more advantages. For example, a patient may be identified more readily in any setting and the patient can avoid having to write extensive information or state information orally when other patients may overhear such communication (which may be embarrassing to the patient). In settings in which the patient cannot communicate, such automatic identification may be especially beneficial.

In one implementation, a computer-implemented method for selectively providing access to medical record information is disclosed. The method comprises receiving, at a computer system, one or more digital images of a healthcare patient from a computing device that corresponds to a user account that is authorized to obtain information about patients in a healthcare system; using computerized facial recognition to identify the person as being one or more registered members of the healthcare system and to obtain a member identifier; using the member identifier to obtain electronic medical record information about the person; and providing some or all of the obtained electronic medical record information to the computing device. Providing some or all of the obtained information can comprise providing critical medical information but not information for identifying the person. The method can also comprise receiving with the one or more digital images, information about the person that has been manually provided by a user of the computing device. Also, the information about the person can comprise information selected from one or more of the categories consisting of gender, size of the person, race of the person, approximate age of the person, eye color, hair color, tattoos, and scars.

In some aspects, the method further comprises receiving, with the or more digital images, metadata that describes a subject of the one or more digital images or a circumstance under which the one or more images were captured, and using the meta data to identify the person as being one or more registered members of the healthcare system. The meta data can comprise biometric data captured from the subject of the images, and the method can additionally include filtering the electronic medical record information using a template to remove information requiring a high level of patient privacy. Moreover, the method can include formatting the electronic medical record information provided to the computing device into a mark-up document containing a previously saved image of the member for comparison to an appearance of the person. The method may further include providing the previously-saved image formatted for side-by-side display with one of the one or more images.

In other aspects, the method also comprises receiving data that is indicative of billable treatment provided to the person, and causing a billing event to be registered with a patient account for the person in response to determining that a billable event has occurred. The method can alternatively or also include processing the one or more images to prevent the one or more images from being reconstructed by a third-party system.

In another implementation, a computer-implemented system for selectively providing access to medical record information is discussed that includes a plurality of digital image capture devices; a front-end server system having an interface to receive one or more digital images from submitting computing devices, and arranged to provide the images for analysis; and a facial recognition server system in communication with the front-end server system and a store of data for digital images that are correlated to members of a healthcare system, the server system programmed to identify matches between faces in the one or more received digital images and face in data for particular ones of the stored digital images. The system can also be provided with a medical record system to provide information about a medical record of a patient in the healthcare system if the facial recognition server system identifies a match between a digital image and a patient in the healthcare system. The medical record system can be programmed to filter information about the medical record so that medical record information provided to particular ones of the image capture devices is matched to an access level of users of the particular ones of the image capture devices. The electronic medical record information can be formatted into a mark-up document containing a previously saved image of the member for comparison to an appearance of the person.

In certain aspects, one or more of the image capture devices comprise smartphone or touchscreen tablets that run applications from multiple application providers. In addition, the system can be further programmed to use meta data received with particular ones of the one or more digital images to identify one or more stored digital images that are best matches for the particular ones of the one or more digital images. Moreover, the meta data can comprise information selected from one or more of the categories consisting of gender, size of the person, race of the person, approximate age of the person, eye color, hair color, tattoos, and scars. The meta data can also, or alternatively, comprise biometric data captured from the subject of the images.

In yet other aspects, the front end server system is programmed to provide to particular ones of the digital image capture devices one or more pre-stored digital images for visual comparison by a user to a person captured by the particular image capture device. The system can additionally include a billing subsystem for receiving data that is indicative of billable treatment provided to the person, and causing a billing event to be registered with a patient account for the person in response to determining that a billable event has occurred.

The details of one or more embodiments are set forth in the accompanying drawings and the description below. Other features and advantages will be apparent from the description and drawings, and from the claims.

DETAILED DESCRIPTION

Figure 1A:
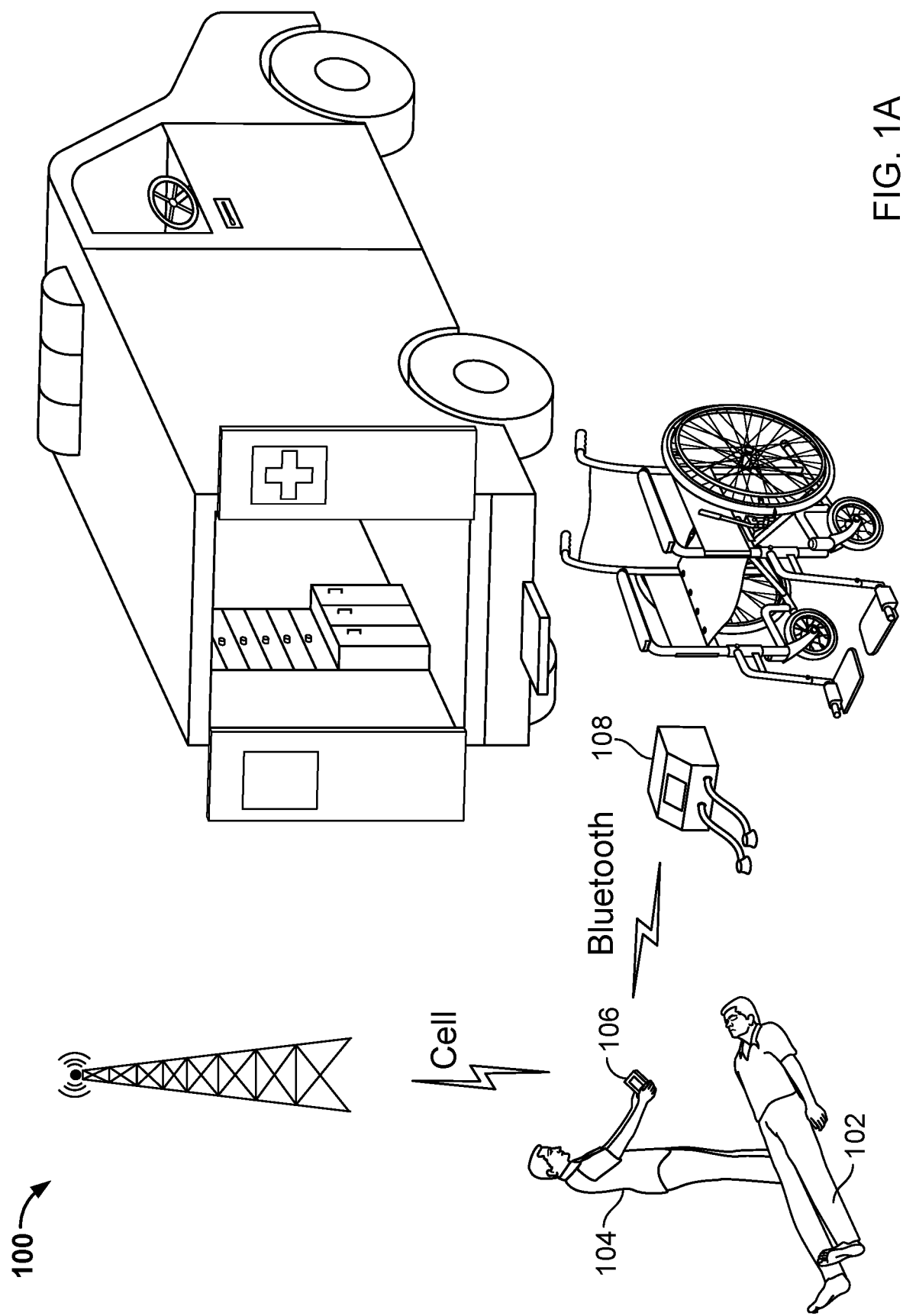
FIGS. 1A-1C show a number of environments in which facial recognition of healthcare patients may be implemented.
Figure 1B:
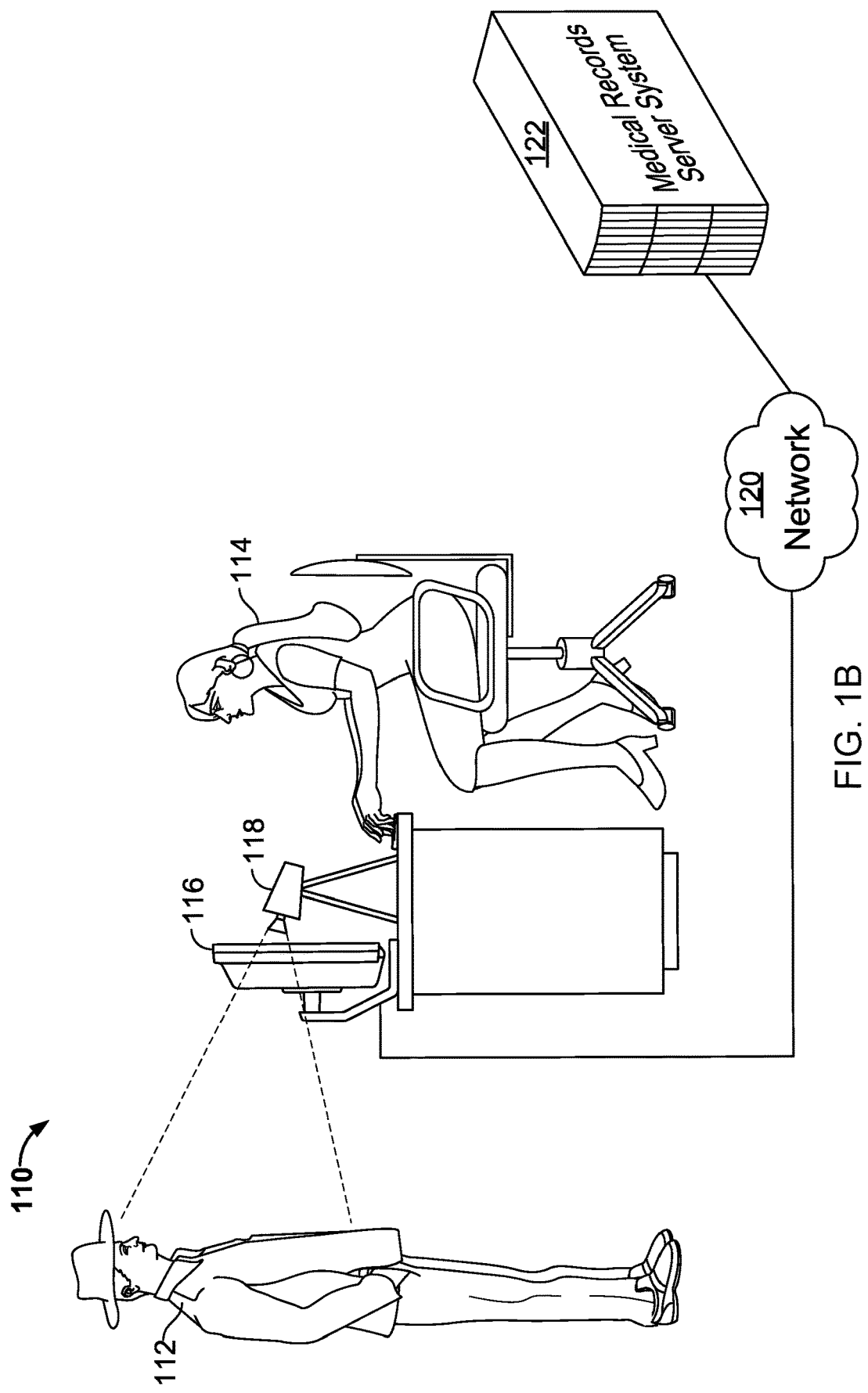
Figure 1C:
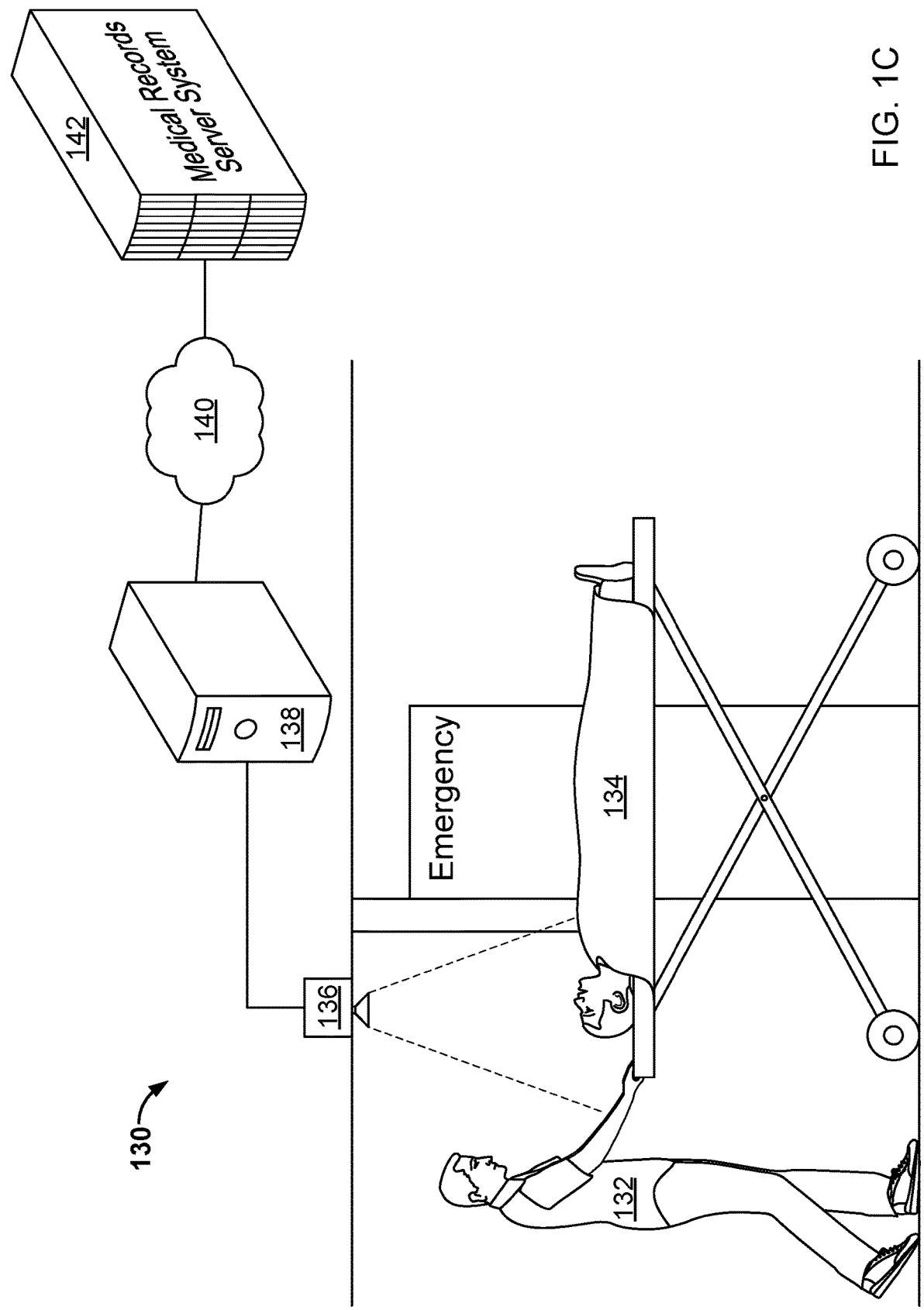

FIGS. 1A-1C show a number of environments in which facial recognition of healthcare patients may be implemented. In general, facial recognition may be used to make more convenient the matching of a presented patient to a patient record, so as to decrease the chances that a patient will be misrecognized and be given inappropriate care. The actions can also enable patient identification when the patient is not able to identify himself or herself, such as when an unconscious patient is admitted to a hospital or other healthcare facility. Such initial identification may be augmented by other data provided by someone who is addressing the patient, such as an admitting nurse or clerk. The information that person provides may include an approximate height of the patient, an approximate age, and other similar information. Also, where the identity of the patient is ambiguous (e.g., where the captured image of a presented patient matches many stored images of patients who are registered with a system), images for all patients who are determined to match may be presented to the person who is addressing the patient, and that person may select one of them from among the group of potential matches. In this manner, patients may be identified quickly, with a level of security, and in situations where identification might otherwise not be possible.

Referring now to FIG. 1A, a scenario 100 is shown in which a victim 102 is being attended to by a rescuer 104 such as an emergency medical technician (EMT). Before the situation shown here, the victim 102 may have been involved in an automobile accident or suffered a sudden cardiac arrest. As a result, the victim 102 is shown here prone on the ground near an ambulance in which the rescuer 104 arrived at the scene. The rescuer 104 may have just arrived at the scene and may have unpacked basic lifesaving equipment such as an external defibrillator/monitor 108. The defibrillator/monitor 108 can take a normal form and may be connected to the victim 102 via various leads so as to measure the condition of the victim 102, including by obtaining ECG readings from the victim 102, and also to treat the victim 102, such as by giving defibrillating shocks to the victim 102.

In this example, the defibrillator/monitor 108 is communicating with a touch screen tablet computer 106 that is being manipulated by rescuer 104. The tablet computer 106 may take a familiar form, and may be loaded with applications by which the rescuer 104 may gather data about the victim 102, may control devices such as defibrillator/monitor 108, and may communicate with other computer users, such as physicians at an emergency room where the victim 102 is expected to be taken. In this example, the tablet computer 106 may communicate with the defibrillator/monitor 108 over a short range communication link, such as a BLUETOOTH link, and may communicate with more distant users over a cellular data network such as the Internet, using cellular 3G, 4G, or similar communication mechanisms.

The tablet computer 106 may also be provided with a digital camera that is integrated with the tablet computer 106 to capture various images from the scene of a rescue. In mass disaster situations, the tablet computer 106 may be used to capture images of the scene to be provided to a central planning facility or to other rescuers who are on their way to the scene. Such images may be used to help organize a rescue effort and to determine the level of response that is needed in a rescue. The camera on the tablet computer 106 may also be used to capture images of the victim 102. In some examples, the images may be used to help identify a condition of the victim 102, such as by taking a full body image of the victim 102 and forwarding the image to a destination emergency room, so that further caregivers may determine what level of care will be needed for the victim 102 when the victim 102 arrives at the emergency room.

The tablet computer 106 may also be used to capture digital images of the victim's face. For example, the rescuer 104 and may take a close-up photo of the victim's face after launching an application for identifying patients for a healthcare provider. The captured image may then be routed through the network to a central server system that may include facial recognition or matching functionality. The central system may have previously indexed and stored images of members of a healthcare system, or the images may be correlated to identifiers for the particular members. Such indexing may include previously-converted images taken of the members, such as at a time when a member checked into a clinic in the system, and creating characteristic points or other mechanisms for characterizing objects in the images to make comparison with other images quicker and simpler.

Identifying information for the victim 102 may also be obtained from sources other than a database held by a healthcare provider. For example, images that are publicly available from a social network (e.g., FACEBOOK) and that may have been labeled by network members with the names of subjects of the images may be analyzed and compared to the captured image for the victim. In such a situation, an image from a social network may be determined to be a probable match for the image of the victim 102 and may be provided on the tablet computer 106, so that the rescuer 104 may confirm whether the person in the image from the social network is the victim 102. Other publicly available digital images may also be used for comparison.

Such matching to the victim 102 may be marked as being only preliminary in the system, until confirmation of the identity of the victim 102 is completed. Nonetheless, the preliminary identity may be used for tracking of the victim 102 through the victim's processing in a health care system until that time.

In response to submitting the visual image of the victim 102, the rescuer 104 may receive a variety of information in return. For example, once the victim 102 is identified by the system 100, an identifier for the victim, such as an account or ID number within a healthcare system, may be used to access a central medical records database for the victim 102. Such access may be complete, in that the rescuer 104 may be enabled to review the patient's entire EMR using the tablet computer 106. The access may also be limited, in that only certain information is determined to be necessary for the rescuer 104 to see, and that is determined to not be of a particularly private nature may be displayed on tablet computer 106. For example, a blood type and known drug interactions for the victim 102 may be displayed, along with important medical history, such as information indicating that the victim 102 is diabetic or has a heart condition. In this manner, the rescuer 104 may be conveniently provided with information about the victim 102 in situations in which the victim 102 is not able to identify himself or herself readily. The rescuer 104 may also confirm, such as by visual comparison of a historical photo with the victim in front of the rescuer 104, that the victim 102 is the person for whom information has been provided.

In certain implementations, the rescuer 104 may use the information derived from taking the victim's photo to communicate with further caregivers in a system. For example, a physician at an emergency room were the victim 102 is to be taken, may have full access to the victim's medical record, and may communicate by typing or by speaking with the rescuer 104. For example, the physician may instruct the rescuer 104 to perform certain lifesaving activities on the victim in a particular way, consistent with information that may be determined from the electronic medical record, and whose disclosure is limited to physicians within a particular health care system, but is prevented from being shared outside such a group.

The identity of the victim 102 may be confirmed in various manners. For example, another person at the scene of an accident may provide a name for the victim, and the name may be checked against information received from submitting the victim's photo to a central system. Also, other biometric data may be taken, such as by obtaining a fingerprint for the victim. In addition, a license plate number for an automobile in which the victim was previously driving, may be submitted and may be checked against state motor vehicle records to confirm an identity for the victim 102. Other similar confirmation techniques may also be used to identify the victim so as to improve treatment that the victim 102 receives from the rescuer 104.

In this scenario and in others discussed below, image matching may also be used to confirm the identity of the person who is seeking access to the patient information. Specifically, such as person may log into the system by having a client device capture their image (e.g., via a front-facing cam), submitting the image data to a central system along with information of who the person is (e.g., a user name). The system may then compare the captured image to a previously-stored image that corresponds to the provided user name. At predetermined time intervals or upon other events (e.g., when a user asks for more confidential information than they have requested previously in a particular session), a system may again require confirmation of the identity of a user in the manner just discussed (e.g., by acquiring another image and comparing it to a long-ago-acquired image and/or to an image acquired earlier in the same log in session). If there is not a match, the system may suspend the session until there is a match (while saving information entered to that point, though perhaps not logging the information into the patient's record in case the entered information was provided by an illegitimate user), and can also generate a message to an account of the putative legitimate user so as to notify that user that someone attempted to access the system using his or her identity and failed to do so. The captured image may also be provided to the real user and/or to security personnel so that they can see who tried to access the system. They may then follow up manually, either to identify someone who attempted improper access, or to help the proper user get into the system where there was a false negative. All captured images may also be saved and be correlated to the patient encounter during which they were captured, so as to permit later auditing of the encounter—e.g., to verify who edited the patient's record.

In other implementations, continuous or near-continuous authentication of a user may be performed. For example, whenever a user is entering information for a patient, a camera on the computer that is receiving the input may be capturing separate images or be capturing frames from a captured video. The images may be checked to determine when a face can be identified (e.g., the user is "squared up" with the camera) and such comparison can be made as frequently as is practical and necessary when a "good" image is available, such as every several seconds. Access can be suspended when there is not a match or if a "good" image of the user's face cannot be acquired for a certain number of seconds while the user is entering data. Again, some or all of the data entered by the user during the session can then be held, and not applied to the actual patient record, until appropriate authorization can be reestablished for the user.

Also, where the automatic facial matching system cannot select a stored image that matches a recently-acquired image with sufficient certainty, all stored images that reach a threshold of similarity may be shown to a user, next to the recently-acquired image, and the user can select one of those images as being the proper patient who was just presented to them. If none of the images is a match, the user may acquire physical identification from the prospective patient (e.g., a drivers license or passport), and may take a picture of, or scan, the identification. That image may then be analyzed and user, either alternatively or in addition to, the prior image data for the patient.

Referring now to FIG. 1B, there is shown a scenario 110 in which a patient 112 is checking into a healthcare facility. The patient 112 may, for example, be checking in for a periodic physical or other visit to a clinic within a health care system. In this example, an intake specialist 114 sits at a desk and is provided with a personal computer 116 connected to a web cam 118 that is positioned to aim horizontally at patients as they approach a counter at which the intake specialist 114 is working. Patients such as patient 112 may thus approach the counter and the intake specialist 114 may direct them to stand in front of the web cam 118 that is connected to the computer 116. A software application executing on the computer 116 may be directed toward capturing patient images and process them in particular manners, such as to save them with a patient's medical record, or to compare them to other images that have previously been taken by the system.

For example, where the patient 112 has not had an image previously captured, the intake specialist 114 may invoke a recording feature of a software application on the computer 116, and may identify the patient by normal mechanisms, such as by having the patient provide a driver's license or other form of physical identification. The image may be then be saved in coordination with the patient 112 record, and a separate subsystem may perform analysis on the image, such as by identifying characteristic points in the image and otherwise providing data that characterizes the image. The patient's processed image data may then be saved in coordination with an ID for the patient for future use.

Alternatively, where the patient 112 has previously provided an image, the intake specialist 114 may invoke features on an application running on computer 116 to capture additional images of the patient 112 for processing. For example, the additional images may be captured and characteristic points or other analysis may be performed on the images, so that data from the analysis may be compared to comparable data stored in a database for the system from prior capture images. Such a comparison may be used to identify who the patient 112 is, and to thereby conveniently pull-up EMR data for the patient 112. Using this technique, a healthcare system may conveniently identify patients as they check into facilities, and may obviate the need for patients to fill out extensive paperwork that identifies them to provide their address and other information. In addition, the system may include a screen that faces the patient 112 and shows the patient 112 information about themselves, so that the patient may readily confirm their identity, insurance information, current home and mailing address, and other appropriate information that needs to be confirmed from time to time. Once the patient 112 is checked in, the EMR data may follow the patient 112 as they move through a particular facility.

A backend system represented by a network 120 in a medical record server system 122 may be employed to assist in the functionality just described. In particular, a network 120 may include a local area network (LAN), a metropolitan area network (MAN), or a broader network such as the Internet, that is employed in appropriate manners by one or more healthcare systems for sharing of medical information within such systems. For example, the medical record server system 122 may store common information needed for the treatment of patients in the system, such as a historical information about previous treatments provided to the patients, personal information about the patients such as blood type, medical history, particular allergies, and other similar information that is commonly stored for patients.

By the use of the network 120 and medical record server system 122, the functionality described here for identifying patients may be extended from a single facility within a healthcare system to multiple different facilities, so that as a patient 112 is arrives in any of the facilities, the patient may be identified using facial recognition techniques.

Images taken of a patient 112 may be used for purposes other than identifying the patient. For example, the web cam 118 may capture visual information about a patient's face outside of the normal visible spectrum, so that the health of the patient may be determined manually or automatically using such a system. For example, images captured of a patient's face may be analyzed to identify the presence of melanoma or other problems with the patient's skin. Also, one image may be compared to previous images to identify a progression of any changes that may occur in the patient's skin.

Such analysis may be done manually, such as by having images of a patient forwarded to a physician or other appropriate caregiver whenever the patient checks into a facility of a healthcare system and is recognized by a facial recognition system, and such analysis may occur in real time so that the patient's primary caregiver may be provided with the analysis before the patient leaves the facility. Such analysis may also occur automatically, such as by an image being provided to an image analysis system that looks for telltale signs of skin disease, and may in turn report to the primary caregiver whether such signs are present. The primary caregiver may then perform more extensive testing and observation.

In scenarios like that shown here, an image that is captured for the patient at the current time may be used as a signature, such as on an informed consent form or other form. As one example, a physician may explain relevant informed consent concepts to the patient, the patient can read the relevant form, and an icon that leads to an image of the patient or a video of the entire process, may be inserted in the signature line of the informed consent form. Thus, if a need arises to review the form, a person conducting the review may select the icon in order to have the video of the interaction (which may be captured by front and rear cameras on a slate computer of the health care provider) played for them, and may see and hear what information was provided to the patient and how the patient reacted.

Referring now to FIG. 1C, there is shown a scenario 130, in which a patient 134 is being admitted to an emergency room on a stretcher. In this example, the patient 134 is again unconscious or otherwise unable to provide identifying information. The patient 134 may have been a victim such as victim 102, and may now be been admitted to the emergency room, such as by being brought in from an ambulance into the emergency room. A caregiver 132 in this example is pushing the patient 134 through a doorway to the emergency room. In certain implementations, the patient 134 is received in a state of altered consciousness, but has previously had their picture captured so that they can be recognized immediately by the system via their face.

In this example, a camera 136 is positioned in a ceiling above the doorway, and aiming downward, so as to capture images of faces for patients who are admitted to the emergency room lying on their backs. In this example, the patient 134 may have previously been identified at the scene of an accident, and the identification at the emergency room at this example may be used to confirm that the patient 134 has arrived. As such, the analysis performed on the patient 134 may simply compare the face of the patient 134 to that previously identified for victims such as victim 102. In such an example, the patient might not need to be identified back to a previously stored image of a patient in a health care system, but may need only to be distinguished from other patients who are set to arrive at the emergency room soon.

In this example, the backend system is shown as including a network 140 in a medical record server system 142 which may be similar to medical record server system 122 in FIG. 1B. In addition, a local server 138 is provided to manage interaction with the camera 136 and the rest of a health care system. For example, the medical record server system 142 may not need to be employed until an identity for patient 134 is determined. Thus, local server 138 may initially cause the image of the patient 134 to be captured, such as by taking a video stream from a camera 136 and analyzing frames of the video stream until a face is recognized as being in the frame using traditional mechanisms. Upon recognizing a face passing camera 136, the local server 138 may provide the image that contains the face, or an image that includes a best capture of the face, to a facial recognition subsystem. The facial recognition subsystem may then return the identity for the patient, and the local server 138 may pass the identity to the medical record server system 142 in order to open a record event for the patient 134.

The local server 138 may also identify a location of the patient (e.g., by correlating the patient location to known, stored locations for the cameras that capture images in a facility), so that the medical record server system 142 passes information about the patient 134 back to one or more terminals in the emergency room. In this manner, information about the patient 134 may appear and be accessible to caregivers in the emergency room substantially simultaneously with the patient 134 passing through the doors of the emergency room. Also, where the patient 134 is matched to the identity of a previous victim at an accident scene, data gathered at the accident scene, such as blood pressure, ECG data, and other data gathered by a system, such as by defibrillator/monitor 108, may also be added to the patient EMR at the time the patient passes through the doors.

In other implementations, the camera 136 may be located in other areas of the hospital and its location may be stored in a computer system so that it can be associated with actions being performed on patients passing by the camera 136. For example, the camera 136 may be located near a CT scanner or MRI machine, and when a patient passes under the camera 136 and is identified by the system 130, the system 130 may check to ensure that the patient is supposed to be receiving an MRI at the identified time. For example, when a face is identified, the system 130 may access a scheduling system for the CT or MRI room and identify one or more patients who are supposed to be receiving treatment in that area around the present time. IDs for those patients may be determined and may then be converted into anonymized image IDs corresponding to images of the patients that have been captured previously, such as when the patients were admitted days earlier. If the image of the patient that just rolled under the camera 136 does not match an image for any of the scheduled patients, an alarm may be sounded so that the technician double checks the schedule and the patient's identity. Also, a check may be made of the medical records of the identified patient to determine, for example, whether the patient has received an implantable cardiovertor or other magnetic implant and an alarm may again sounded to prevent such a patient from entering an MRI room.

Similarly, identification checks like those discussed here may be used before giving a patient a critical medication, including expensive medications or dangerous medications (e.g., insulin). In such situations, a test or procedure may be ordered for a patient, and a stored image of the patient may be printed on the order form that the technician who performs the test or procedure is given. The technician may then use the photo as a manual check, in addition to the system automatically acquiring an image of the patient's face and making an automatic confirmation. Thus, one confirmation may back up the other one. A screen on a tablet computer or a display outside a room where a test or procedure is to occur, may provide a graphical representation indicating whether the patient who has arrived has a face that matches stored data for the patient scheduled for the current time. If there is a match, for example, a green smiley face may be displayed along with descriptive textual information. If there is a failure to match, a red face with an "X" through it may be shown, along with explanatory text.

Recognition techniques similar to those discussed here can also be used in additional areas, where a system could implement one or more of the techniques discussed above, and also use image recognition for additional purposes. In some such circumstances, the image recognition system can be made independent of the particular use to which it is put, and may return identifiers of matching faces in images, without concern for how another sub-system uses the match information.

As one example, systems like those described here can use facial recognition for allowing users to log into a computer system. For example, a matching system can be loaded with images of patients and with images of employees in a system, and a matching sub-system may simply return an identifier for the image that generated a match, and the receiving system may then use the identifier in order to determine who the match was (e.g., it can use the identifier to generate an ID number and then try to match that ID number against ID numbers for all employees in a healthcare system who are authorized to use a particular computer or type of computer, or who are authorized to access particular records).

In some instances, facial recognition may also be used to maintain a logged-in state for an employee. For example, a system may be set to log a user off after a preset number of minutes of inactivity. Facial recognition may be used so that the system checks for the presence of a particular face in front of the computer (e.g., via a web cam) and if the face is not found for a predetermined number of tries or predetermined time period, the computer may lock up or log the prior user off (which may be particularly useful for computer terminals that are located in public or shard areas of a facility).

The presence of a particular user's face in front of a computer may also be checked at predetermined points in time in order to provide authentication for certain actions. For example, when a record is submitted, the user may be checked (e.g., by capturing an image with a web cam and comparing it to a stored image for employees or a particular employee) to confirm which user submitted the record. Such an approach may prevent the use of a "scribe," who might take over after a particular user logs in. Such biometric checking may be enforced at any point in a process where the presence of the particular user is important.

Also, such systems may be able to alert law enforcement, social service, or other authorities to the presence of a "John Doe" patient. For example, if a patient with dementia is admitted and the patient's face does not match any relevant databases, an image of the patient's face may be transmitted to law enforcement authorities, as they are most likely to be contacted by family members who might report a missing person.

Such systems may also be used to augment security for babies and minors. For example, facial matching by parents (and perhaps babies) may be required in a nursery before a baby can be removed. Also, images taken for such matching may be stored for a predetermined period (e.g., a day or a week) in case there is a report of improper activity relating to a baby. Similarly, minor patients may be imaged as may their guardians (e.g., their parent or parents) when they are checked in, and the patients may be released only into the care of a guardian who has previously been imaged. The identity of the guardian may be matched against a previously acquired image from the check in time, either manually or automatically in the manners described here.

Also, the patient's current image may be appended to medical paperwork and also displayed above the patient's bed or on the patient's wrist band, so as to decrease the chance that a caregiver will provide care to the patient that is intended for another patient. Moreover, the facial capture may be used to augment or replace signatures for forms, consents, and other procedures.

In another example, a patient may use an image captured on his or her home or portable computer so as to access his or her own medical records. For example, the user may log into an account and may submit a real-time captured image, which may in turn be compared to stored image data such as in the manners discussed above and below, and the user may be provided with access to his or her records only if there is a match. Multiple different images may also be required (or images in a video stream) in order to establish that the user is not simply holding a photo in front of the web cam.

Also, the capturing of a patient image may be required at various points in the treatment cycle in addition to those discussed above. For example, a match of a real time image to stored image data may be required whenever a serious procedure is performed on a patient, such as the administration of drugs, insulin, giving of blood, and the like. The confirmation of a facial match may be saved so as to provide an audit trail for such actions being performed and confirmed with the patient.

Also, the digital camera may be a user-facing camera on a smartphone or similar mobile device. For example, if a physician is speaking to an assistant on a smartphone, an image may be captured of the physician and stored or compared to preexisting image data for physicians in a healthcare system in order to verify that actions subsequently taken by the assistant were likely authorized and directed by the physician. Similarly, a family member who is given consent may have their image captured (or a video captured), and a healthcare provider may review it before it is saved—such as when the family member is providing consent for a particular procedure. Thus, the entire conversation for the informed consent may be recorded digitally, and automatically stored in association with the patient records so that it may be retrieved later for auditing or investigation purposes.

When such conversations are recorded, additional information may be displayed on one or more of the users' devices and such data may also be capture with the video of one or more of the users such as by capturing a video screenshot of the family member's device. Thus, for example, text may be shown to a family member or patient or other user, while a conversation is occurring with a caregiver, and the user may be asked to confirm a course of actions that corresponds to the displayed information, such as by displaying an instruction "Please press the icon below if you confirm that the patient may be provided with [description of care]."

Figure 2A:
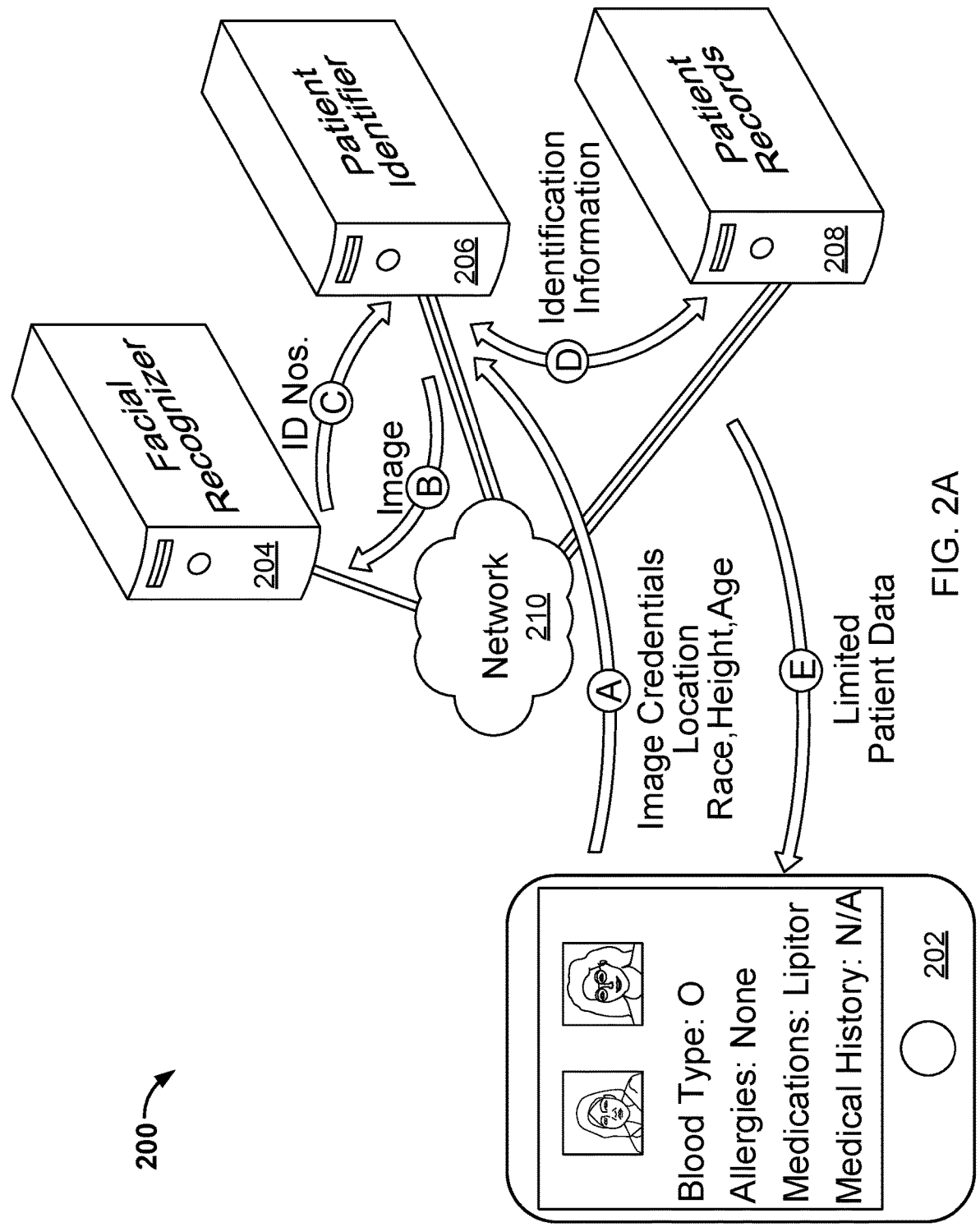
FIG. 2A is a schematic diagram of a system for providing patient information in response to receipt of one or more images of a patient.

FIG. 2A is a schematic diagram of a system 200 for providing patient information in response to receipt of one or more images of a patient. In general, the system 200 includes a number of subsystems arranged to communicate with and cooperate with each other in order to provide integrated facial recognition in a medical records and billing system. The subsystems may each have assigned roles in the overall system 200 and may communicate with each other according to application programming interfaces (APIs), by which each subsystem may communicate relevant information to other subsystems in the overall system 200. Although a particular arrangement of a client and several servers is shown in this figure as an example, other arrangements may also be provided, wherein various mobile or other computing devices may serve as clients, and various servers or arrangements of multiple servers may act as the servers in the system. The use of the terms "client" and "server" here are simply meant to indicate devices or subsystems that receive service from other devices or subsystems, or provide such services, and is not intended to limit the system 200 to a particular formal client/server arrangement.

In the system 200, a mobile computing device 202 asks to obtain information about a patient in a health care system. The device 202 may take a variety of forms, including a tablet touchscreen computer, a smart phone, a personal desktop computer, and other appropriate forms. The device 202 may include or be connected to a digital camera for capturing images, including images of a face of a prospective patient in a health care system. The device 202 may also include a number of additional applications to cooperate with the facial capture application, which may be a standard camera application on the device that communicates with the other applications by a published API for the device 202.

Certain of the applications running on the device 202 may be configured to permit processing of prospective and actual patients within a health care system. For example, an enrollment application may be used to check in a patient and verify that the patient is a member of the health care system. A patient record application may be used to provide EMR information about the patient once they have been verified. In addition, the medical records application may allow a user of device 202 to input additional information about the patient and have that additional information saved in the patient's medical record. A billing application operating on the device 202 may interface with the medical record application or with a medical record server in order to identify billable events in the treatment of a patient. For example, if a medical record indicates, by the input of a billing code by a caregiver, that the patient has received a particular type of care, a billing entry may be generated by the system 200 for the patient with respect tobacco. Such an event may then be stored by a billing system so that a bill for the care provided to the patient may be generated periodically and provided to a payor for the patient or to the patient.

A number of server subsystems communicate with the device 202 by way of a network 210. The network 210 may take a variety of forms, and may include, without limitation, a LAN and one or more portions of the Internet, where communications over the Internet may be provided in a secure manner so as to protect privacy of a patient in a health care system. A first server subsystem is a patient identifiers server 206. The patient identifier 206 is a system that may be operated by a health care system and may coordinate efforts to identify a particular incoming patient as a member of the health care system or to otherwise identify the patient. The patient identifier 206, in a traditional manner, may receive input that indicates a patient ID number within the system. In such a situation, a patient identifier 206 may provide the ID number to a patient records subsystem or server 208 for provision of patient records to a caregiver of the patient.

In other implementations, the patient identifier 206 may receive a digital image for the purpose of identifying a prospective patient. The digital image may then be provided by the patient identifier 206 to a facial recognizer 204. The facial recognizer 204 may be a system operated by a third-party, and may thus be provided with limited information from the patient recognizer 206. For example, the patient identifier 206 may simply pass the digital image and a session number that may then be passed back by the facial recognizer 204 when it makes a determination about the digital image. To provide even greater privacy, the patient identifier 206 may provide data that cannot be reconstructed into an image, such as a hash representation of the image, where the target space for the hash is sufficiently large to provide recognition between different images without excessive false positives or false negatives.

The facial recognizer 204 may be programmed with processes for making determinations of matches between data for two different images, particularly with respect to facial characteristics of individuals in the images. The facial recognizer 204 may have access to, or may have been previously provided with, data characterizing images of the faces of members of the health care system. Such data may serve as a baseline for the comparison with subsequent data provided by the patient identifier 206. When the recognizer 204 identifies a match, it may provide back to the patient identifier 206 a session identifier and an ID number for the matching file. The ID number may be used by the patient identifier 206 to determine what patient the facial recognizer 204 determined was a match. In particular, when the facial recognizer 204 was first given the data for the matching figure, it may also have been given an ID number by the patient identifier 206 or by the system working with the patient identifier 206, where the ID number corresponds in the patient identifier 206 to a particular patient in a system. In this manner, the connection between a particular patient and image data for the patient may be kept at the patient identifier 206, and not shared with the facial recognizer 204. As a result, the facial recognizer 204 may be provided by a third party without substantial concerns for privacy issues or other data security issues.

The patient records subsystem 208 may then communicate with the patient identifier 206 to provide information about the particular patient to the mobile device 202. In particular, the patient identifier 206 may pass to the patient records subsystem 208 an identification number for a patient, along with an identification number for a caregiver who is using device 202. For example, a user of the device 202 may be required to log into the system 200 for each session that the user of the device 202 instigates, and the user may have a role that grants them access to particular information but not to other information. As one example, an EMT may be provided access to patient information that is necessary for providing emergency care, but not to deeper information about a patient's medical history. In contrast, a physician may be provided with more data, and a terminal identifier (for the computer that is being used to access the data) may also be provided to the medical record system so that, for example, only caregivers accessing a patient's records from within a physical facility within a health care system, and having top access credentials, may access the most private information about a patient. In this manner, the system 200 can ensure the physical security for access to highly confidential information.

Where appropriate credentials have been provided by a caregiver through device 202, the patient records subsystem 208 may provide information requested by a user of the device 202. For example, an initial query may result in the patient records subsystem 208 providing identification information for the patient, along with basic vital information such as blood type. Such information may be provided in the form of markup language, such as extensible markup language (XML) according to a healthcare industry-specific format. An application on the device 202 may be programmed to display such information in a useful manner, such as in a graphical user interface (GUI) that is part of the device 202, via a browser-based application of a standalone application, or app.

Subsequent interaction by a user with device 202 may result in additional information being provided from the patient records subsystem 208, or being provided to the patient records subsystem 208. For example, the device 202 may communicate wirelessly with a patient monitor to record activity such as ECG readings for the patient, and such readings may be automatically uploaded to a record for the patient in the patient records subsystem 208. Later, such information may be downloaded by a physician who is treating the patient later in the day to determine the condition of the patient at the first moment in time.

A particular example process flow for the system is shown by lettered arrows in the figure. The process begins with Arrow A, where the mobile device 202 captures an image of a patient and transmits data for that image to the patient identifier 206. The data for the image may be accompanied by credentials that indicate an identity of the user of mobile device 202, such as by including an ID number for mobile device 202 or information from a cookie stored on mobile device 202, that can associate the mobile device 202 with a particular user account with the system 200. Other metadata may also be passed to further characterize the patient. For example, information regarding the location at which the image was captured may be provided, as may information about the race, approximate height, and approximate age of the patient. The latter information may be entered on a form by the caregiver who is using device 202. The location information may also be provided by the caregiver, or may be obtained automatically from the device 202, such as using GPS functionality on the device 202, or by using cellular tower triangulation techniques.

The extra metadata may be useful in disambiguating matches performed by the facial recognition system. For example, the patient identifier 206 may access data about the home locations of members of a health care system when multiple images are determined to be a match with an image supplied by device 202. A patient whose home is closest to the current location of the device 202 may be preferred in a match over other patients. Similarly, medical record data may indicate a race, height, and age for a patient, and that data may be compared to information entered by a user of device 202.

At Arrow B, the image and other relevant information may be passed from patient identifier 206 to facial recognizer 204. In one embodiment, the information passed may be a representation of the image, such as an image file, or a hashed version of an image file. Also, characteristic points data may be determined by the patient identifier 206 and passed to the facial recognizer 204, or such data may be generated from by the facial recognizer 204. A session ID may also be passed so that the patient identifier 206 may correlate data that is returned from the facial recognizer 204 in an appropriate fashion.

At Arrow C, the facial recognizer 204 passes back to the patient identifier 206 one or more identification numbers or other appropriate values to identify which images stored at the facial recognizer 204 were matched to the provided image. The IDs may have been previously generated by the patient identifier 206 or a related system, and may be correlated at the patient identifier 206 with patient IDs. Such correlation may be one to one, so that the patient identifier may use the IDs received from the facial recognizer 204 to obtain IDs for the patient within the medical record system. At Arrow E, the patient identifier 206, after performing a lookup or similar operation, passes the patient IDs to the patient records subsystem 208. Other information may also be passed, such as an identifier for the user of device 202. In addition, an IP address for the device 202 or other mechanisms by which patient records subsystem 208 may communicate directly with device 202 may be passed.

At Arrow E, limited patient data is passed from the patient records subsystem 208 to the device 202. For example, the user of device 202 may have been identified as an administrative worker within a health care system, and not a physician or attending nurse. As a result, only limited information may be provided to the person, and information that is not needed to perform the role that is held by the person may be withheld.

Using the system 200 and the process described here, caregivers within a medical system may conveniently and automatically identify patients quickly and/or in situations where the patient is not capable of identifying themselves. In addition, such identification may be useful to identify users of a health care system who are passing themselves off as a different patient, such as drug seekers. In such a situation, a system may determine that a single person is attempting to access prescriptions for drugs simultaneously under aliases, and may permit a caregiver to compare information for the two patient aliases and take appropriate action as necessary.

In addition, although not discussed in detail here, other biometric data may also be taken from a patient. For example, retinal scans may be taken in particular situations, as may fingerprint readings. For example, a blood oxygen monitor may be supplemented with a fingerprint scanner so that when it is placed on a patient's fingertip, it both monitors the patient's blood oxygen and also is able to help identify the patient.

Figure 2B:
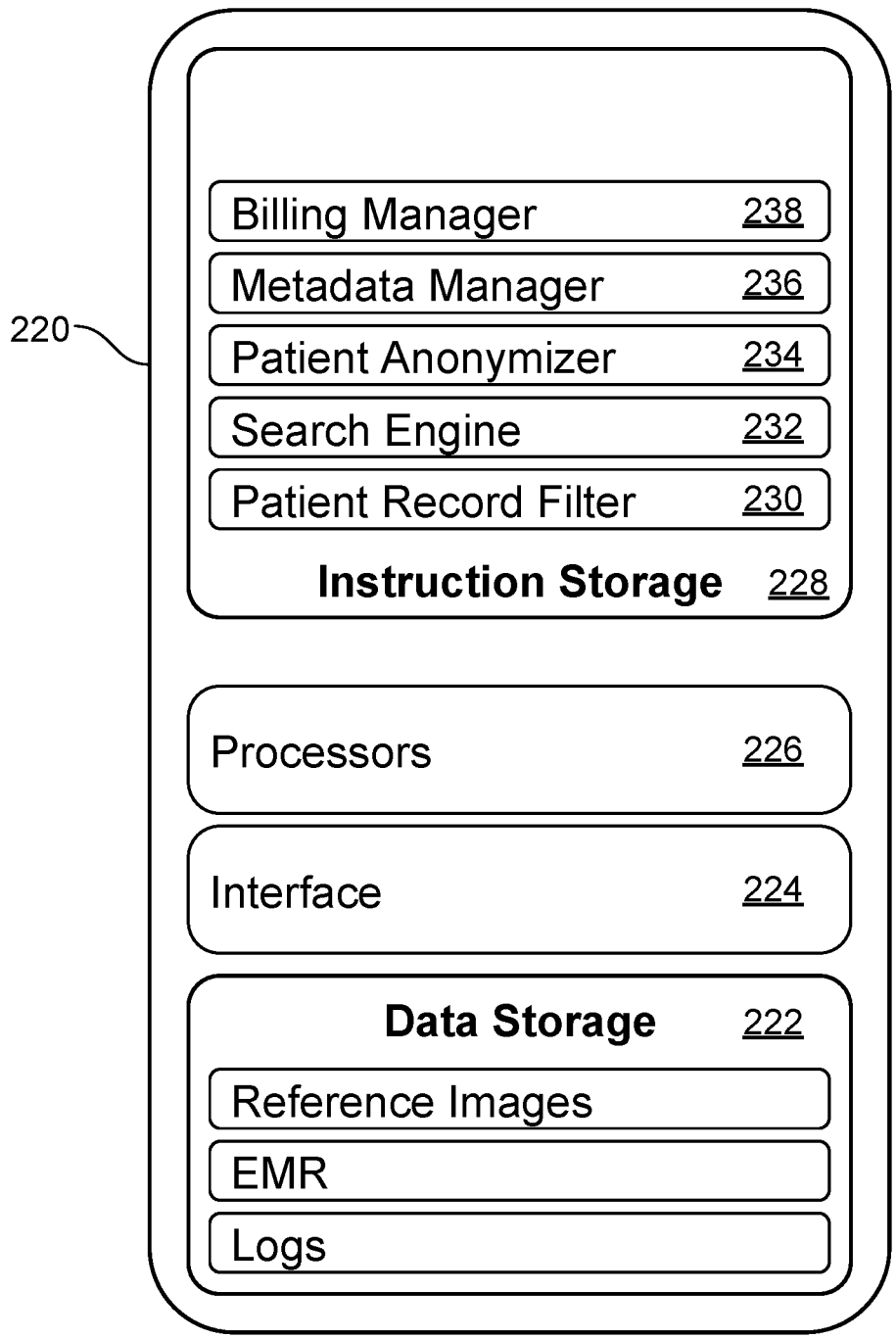
FIG. 2B is a block diagram of an example computer system for managing information retrieval in response to the provision of one or more images of a patient.

FIG. 2B is a block diagram of an example computer system 220 for managing information retrieval in response to the provision of one or more images of a patient. The particular modules shown here in the system 220 are provided as examples of components that may be present in an example overall system, such as system 200 in FIG. 2A, and the particular modules may be implemented in various different manners, and on one or more different machines. For example, certain of the modules may be implemented on one or more client devices that are used by healthcare providers, while others of the modules may be implemented on one or more server systems, such as a server subsystem shown in FIG. 2A.

Starting at the top, the system 220 may include a number of executable modules in instructions storage 228. The instructions storage 228 may store software instructions that may be loaded onto a processor or processors 226 and executed by the system 220. The storage may occur on permanent or temporary memory, such as hard disk drives, flash memory, DRAM, flash storage, and other similar memory mechanisms.

A billing manager module 238 tracks activities performed with respect to a patient and for which a billing event may be recorded. For example, each time a caregiver gives care to a patient, a billing event may be recorded. Also, supplies provided to a patient, such as drugs, bandages, and other supplies may also be recorded with the billing manager 238. The billing manager 238 may track such activities and may accumulate billing events for each of a number of patients in a health care system. At periodic intervals, the billing manager 238 may generate bills to be provided to patients or payors associated with the patients.

A metadata manager 236 may store data about patients or caregivers relating to images captured of patients or potential patients. For example, the metadata manager 236 may associate the one or more pieces of data with a particular file that represents an image taken of a patient or potential patient. The metadata may include, for instance, latitude and longitude data that indicates where a particular image was acquired, along with data that describes the person shown in the image.

A patient anonymizer 234 may provide for the tracking of patient images while preventing personally identifiable information about a patient from being determined outside of a core healthcare subsystem. For example, the patient anonymizer 234 may convert a patient name or a terminal ID number to an external ID or session number to be used with systems external to the main system. The anonymizer 234 may also convert image data in various manners so that the image cannot be rebuilt and viewed by someone outside the core system. As one example, the patient anonymizer 234 may hash image data to provide to another system in a manner that the data still indicative relevant features of the original image, but from which the original image cannot be reconstructed. Fingerprints may then be formed from the converted data, or the converted data itself may serve as a fingerprint of the image, for comparison of one image to another for image matching purposes.

A search engine 232 may be provided with the system 220 in order to return search results in response to research received search queries. For example, the search engine 232 may receive an image or data characterizing an image, and may compare it to pre-stored images or data characterizing pre-stored images, and may return various images that are a closest match to the provided image. The returned results may be provided in a ranked order from most relevant to least relevant, and a numerical or similar indication may be provided to indicate the degree of match between the query and a particular result. For example, an arbitrary percentage value may be assigned, where higher percentages indicate a higher match, so that a percentage may indicate a match between images only if the number is higher than 90% or another selected number. In this manner, a user of a system may adjust the degree of match required before the system will trigger a match between images, and may thereby control the number of false negatives or false positives in the system.

A patient records filter 230 may act to limit the amount of patient information that is provided to a particular requester. For example, as described above, lower-level medical personnel may not need access to a full medical history for a particular patient. The patient records filter 230 may thus store information that correlates a particular caregiver to a role for that caregiver (e.g., physician, EMT, administrator, etc.), and may also have defined with it access rights for particular roles. For example, one caregiver may be an emergency room physician and may have full access to a patient's records, particularly when the physician is logged in from a computer in a secure premise, such as at an office in the emergency room. In contrast, an EMT may have lower rights and may be allowed to look only at critical data such as blood type and similar information needed in an emergency scene.

Processors 226 may operate within the system 220 and may execute instructions from the instructions storage 228. The processors 226 may be standard microprocessors and associated supporting chip sets organized to execute code that is stored on the system. The processors 226 may receive data during their operation by way of one or more interfaces 224. The interfaces 224 may execute application programming interfaces (APIs) so that various subsystems can communicate conveniently with each other in certain instances, such communication may operate by means of remote procedure calls (RPC) internal to a system, while in others, the communications may occur by way of HTTP requests and corresponding responses (e.g., where an interface is implemented by a web server).

The processors 226 may store data that is generated by the various processors in data storage 222. For example, reference images 240 may be stored by one subsystem and may be represented by data that characterizes a number of images that have previously been taken of members in a health care system. The images 240 may be in their original format as captured by a camera digitally, or may be converted in one or more ways to improve the ability to compare different images to determine whether there is a match in images. For example, characteristic points in images may be identified to form fingerprints for each of the images, and the fingerprints may be stored and later compared in familiar and known manners.

An electronic medical records (EMR) module 242 is provided to store information about particular patients and the medical histories for those particular patients. The processors 226 may, for example, access the information from the EMR 242 and provided that information to other subsystems in the system 220, or may identify new information for a patient (e.g., where the patient is currently being monitored by a caregiver and/or piece of medical equipment) and may update the EMR 242 accordingly.

Logs 244 store information indicating chronologically-sorted activities within the system 220. For example, the logs 244 may indicate caregivers that of access the system 220, and the information that they have accessed, along with time stamps and related information. For example, when a user of a mobile computing device captures an image of a potential patient, the logs 244 may add a record that stores information about such a transaction, such as identifier for the caregiver, a time that the request was made, and an indication of the type of information or content that was provided back to the caregiver.

Using such a system 220, simplified an automatic facial recognition technology may be provided within a medical record system, and may be integrated with additional portions of a healthcare information system, such as a billing system. For example, a patient may be identified using facial recognition, may have medical records retrieved based on such a determination, and subsequent care may be provided to the identified patient a simple and relatively automated manner.

Figure 3:
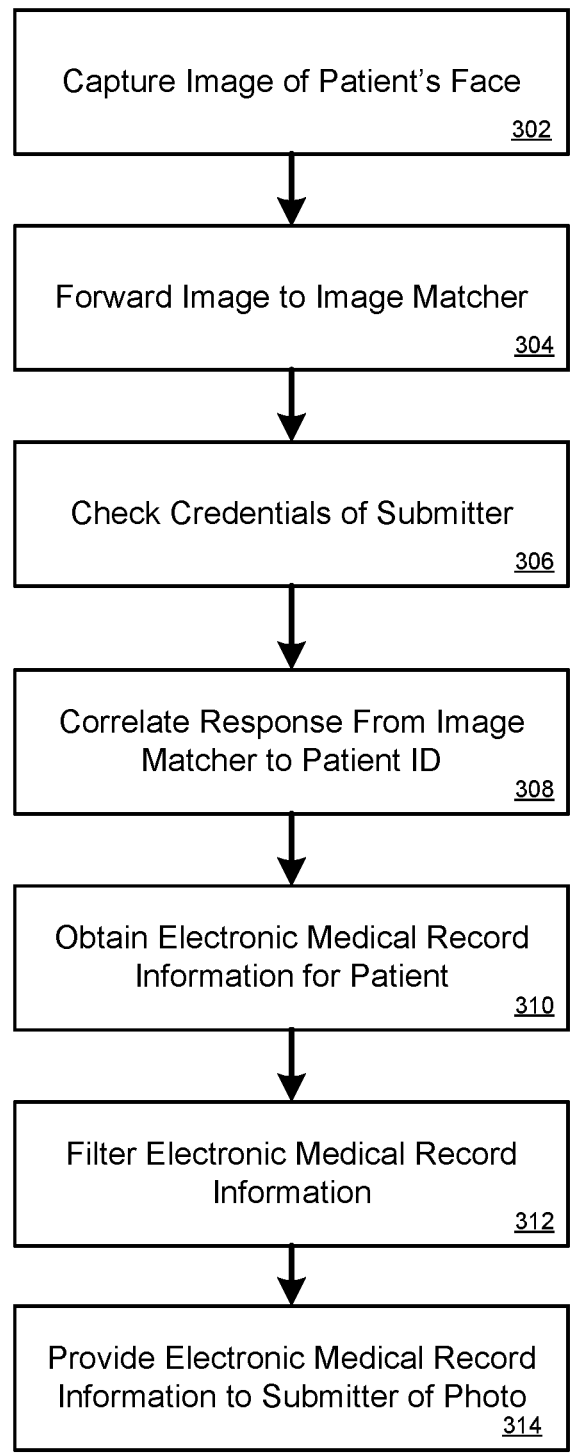
FIG. 3 is a flowchart of an example process for providing medical record information in response to receipt of an image of a patient who is enrolled in a healthcare system.

FIG. 3 is a flowchart of an example process for providing medical record information in response to receipt of an image of a patient who is enrolled in a healthcare system. In general, the process involves capturing an image of a potential patient for a healthcare system and identifying the potential patient by comparing data from the image to data from other images that have been previously captured by the system. Upon identifying the potential patient, medical record information may be gathered for the patient, and billing activities may occur with respect to care that is given to the patient.

The process begins at box 302, where an image of the patient's face is captured. The image capture may occur according to one of the examples indicated in FIGS. 1A-1C, or in other appropriate manners. The image may be processed at the point of capture or at a later point in various ways. For example, facial identifying software may be used to locate a face in the image, and to crop the image or otherwise remove components of the image that do not include the face of the potential patient. In addition, the image may be transformed from its native format, such as a JPEG format, into a format that can be analyzed for comparison purposes. As one example, the image data may be run through a one-way process, such as a hash, in a manner that maintains relevant image data that can be used to identify particular features within the image, but that anonymizes the image or shrinks the amount of data that needs to be stored and processed.

At box 304, the image is forwarded to an image matcher. Such forwarding may occur in various manners, including by sending the image data to an intermediate system that in turn sends the image to the image matcher. The image may be accompanied by various metadata, such as data that indicates a location at which the image was captured, a gender of the potential patient, and similar information.

At box 306, the credentials of the submitter are checked. Such a step may occur initially upon the submission of the image, and may involve determining that the electronic device that submitted the image data has been appropriately logged into a system with a user name and password of a user that is registered with the system. Credentials may be stored for a period on the device, such as in a cookie or other similar mechanism, though the credentials may be set to expire after a period that is sufficient to provide for convenient use by a caregiver and yet prevent unauthorized users from gaining access to the system.

At box 308, the process correlates a response from the image matcher to a patient ID. For example, the image matcher may identify another image in its pre-stored database, which have been taken at previous points in time for members of a healthcare system, and may pass back an identifier number for that image. The image matcher may also have used some of the metadata in making the determination regarding the match, and may match that to meta data received with he image of the prospective patient in order to generate a more complete, composite score indicating a degree of match.

Where the image matcher stores a form of the image data that permits reconstruction of the original pre-stored images, the image matcher may pass such data back to the originating device or to an intermediate subsystem. Alternatively, where the image matcher does not store a reconstructed old version of the image, the intermediate subsystem may store such an image. The original stored image may be used in various manners, such as by providing it back to the originating device, so that a user of the originating device may confirm that the match is truly accurate, before proceeding to treat the potential patient in any manner.

At box 310, electronic medical record information for the patient is obtained. For example, an intermediate subsystem may correlate an image identifier from the image matcher to a table of stored patient ID's, and may submit an identified patient ID to a medical record system in order to obtain medical record information about the patient in the system who has been determined to be a match for the prospective patient in the captured image.

At box 312, the process filters electronic medical record information from what that is obtainable from the full medical record for the patient. For example, an intermediate subsystem may use the credentials of the submitter to determine what level of access the submitter should have to patient information. The intermediate subsystem may then request from a medical record system only data about a patient that matches that determine the level of axis.

At box 314, the process provides electronic medical record information to the submitter of the captured image or photograph. The medical record information may initially include basic medical information for the potential patient, and may be accompanied by the pre-stored image of the matching patient in the system. In this manner, the submitter who is operating the initiating device may look at the pre-stored image and compare it to the patient who is in front of them to confirm that the person in front of them is truly the patient that has been identified by the system.

In addition, the submitter may interact with the system in various ways after receiving the initial patient information. For example, the submitter may request additional patient information, and the particular type of information requested may depend on the condition of the patient and the particular needs of the caregiver, just as ordinary access to medical record systems may depend on the particular situation. As the caregiver treats the patient, the caregiver may also enter codes indicating treatment that is been given, and those codes may be linked by the process to billing actions. Those billing actions may in turn be linked to records for the identified patient, and may be stored in a billing system in association with the patient. Such association made later be used by a query in generating a bill for the patient, such as by searching for all actions associated with billing that include the patient's ID number in the relevant field.

Figure 4:
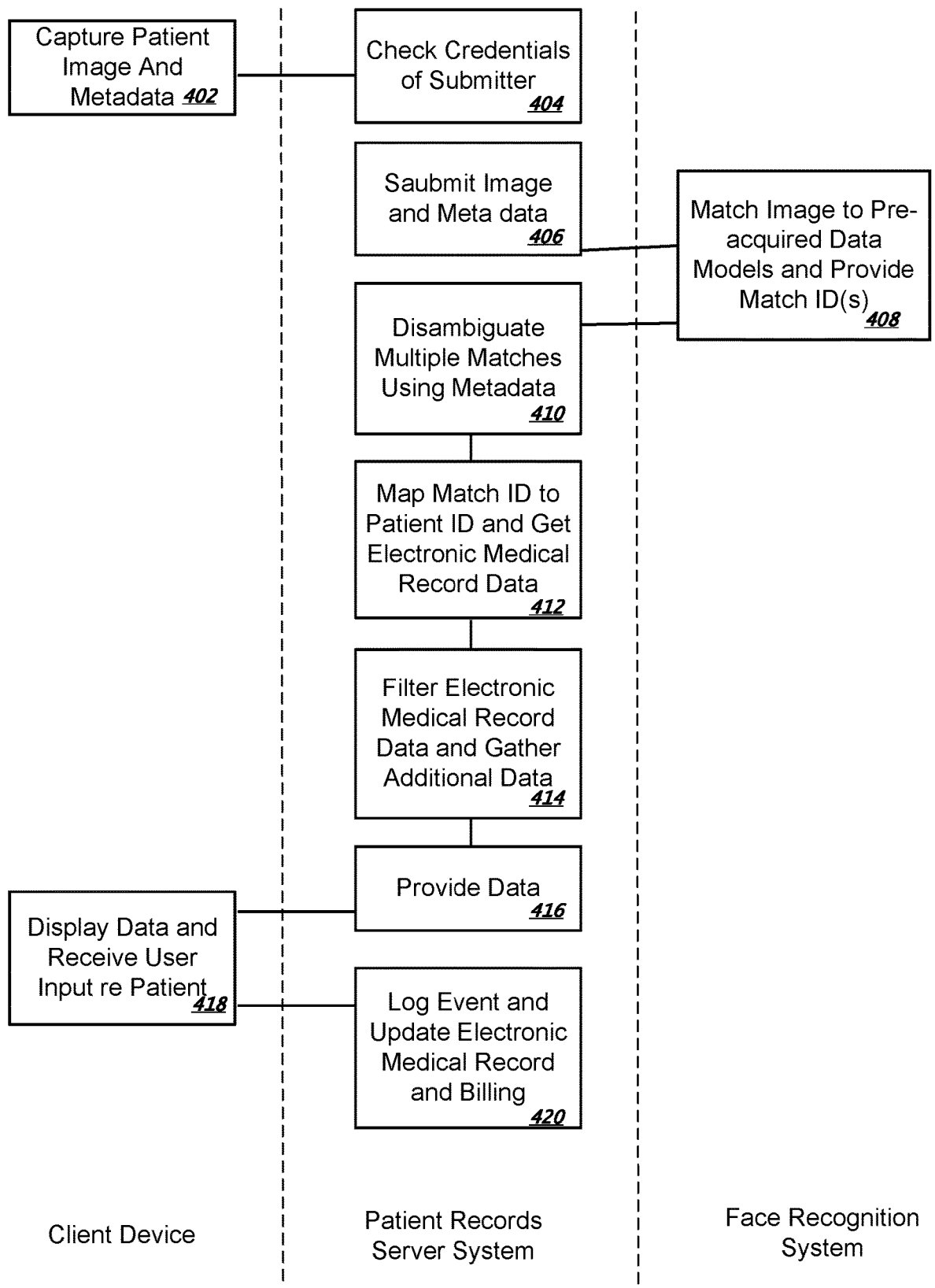
FIG. 4 is a swim lane diagram that shows example interactions between components of a facial recognition system.

FIG. 4 is a swim lane diagram that shows example interactions between components of a facial recognition system. In general, the process shown here is similar to the process in FIG. 3, but is shown more specifically in this example as occurring on particular subsystems in a larger system, so as to provide greater clarity for one manner in which the process may be carried out.

The process begins at box 402, where a client device captures a patient image and metadata relating to the patient. The image may be captured, for example, on a camera that is integrated with the client device, such as on a mobile computing device in the form of a smart phone. The image may also be accompanied by metadata such as information indicating where the image was captured, and other information about the patient that may not be readily apparent or analyzable by a computer from the image.

At box 404, a patient records server system checks credentials of the user or device that submitted the image and metadata. Checking of credentials may occur by familiar mechanisms, including by determining that the client device has previously logged in to the patient records server system during the current session. At box 406, the patient records server system submits the image data and the metadata to a face recognition system. The separation of the patient records server system from the face recognition system in this example may enable a specialized high-powered face recognition system to be used and accessed, such as a system provided a third-party that specializes in facial recognition activities. The use of an external system, however, may compromise privacy, so that the data provided to the face recognition system may be anonymized in various manners to maintain that privacy. For example, a tracking number, such as a session ID, that is provided from the patient records server system to the face recognition system may be selected so that the data may not be used to determine the identity of a patient. Also, the image data may be pre-processed so that the image cannot be reconstructed in visible form by the face recognition system.

At box 408, the face recognition system matches the submitted image with pre-stored image data (e.g., captured by taking pictures of members of a healthcare system when they previously checked in for visits in the system or otherwise enrolled in the system) and provides match IDs back to the patient records server system. Such matching may occur by way of various image matching algorithms, and may include identifying characteristic points in an image.

At box 410, the patient records server system receives from the face recognition system a plurality of potential matches for the provided image. Thus, the patient records server system may disambiguate those multiple matches using metadata that was received from the patient image. For example, the patient records server system may use identifying numbers for each of the pre-stored images that is determined to be a match, to pull corresponding metadata from a patient records database, such as gender, weight, age, and height information. In addition, information about the home addresses of the patients whose pre-stored images have been identified by the face recognition system may be determined. Such determination may occur, of course, after converting an image ID number from the face recognition system to an internal patient ID number for the patient in the patient records server system. A best match may be determined using a combination of the image mapping score, and the metadata matching scores, and if a sufficiently high likelihood of matching is determined by the patient records server system, the process at box 412 maps the matching ID to the patient ID to get electronic medical record data for the identified patient. As a manual check on the matching, the matched image may be provided back to the client device for display to a user of the client device, and the user may be prompted to confirm whether the matched image from the face recognition system is truly a match to the patient in front of the user.

At box 414, the patient records server system filters electronic medical record data and gathers additional data for providing to the client device at box 416. For example, the medical record for a patient may indicate that the patient has a particular rare form of disease. The patient records server system may present such information to the client device, and may also gather information from online database that indicates how patients with such a rare disease are to be treated in particular situations (e.g., when they are bleeding). As a result, a user of the client device, at box 418, may have the data displayed to them, and the client device may receive from them user input regarding the patient. For example, a caregiver may enter vital sign information about the patient, and sensors such as heart rate and ECG sensors that are plugged into a smart phone or other client device may automatically provide such data back to the patient records server system. Thus, at box 420, the patient records server system logs the event and updates the EMR and billing record for the identified patient. Such logging and updating may occur in a variety of ways and maybe be performed using patient identification plug-ins that may be provided as an adjunct to an existing medical record and billing system.

In this manner, the process just discussed conveniently integrates operations of various sub-systems, including existing medical record and billing systems, and new facial recognition and patient identification systems. Such integration may also occur using common mobile wireless devices that caregivers are accustomed to using in their ordinary lives for communicating and computing. The integration may be accomplished so that a caregiver and a patient need not spend time entering large amounts of data into a system. In addition, the process may be implemented in a secure manner by controlling the level of information about patients that is made available to certain subsystems.

Figure 5A:
FIGS. 5A-D are screen shots of example displays that can be provided with a medical-based facial recognition system.

FIGS. 5A-D are screen shots of example displays that can be provided with a medical-based facial recognition system. FIG. 5A, for example, shows a display of an EMR patient record that has been supplemented with images of a registered patient 500 and a prospective patient 502. The image of the registered patient may be an image that was previously captured when the patient 500 checked into a system with identification such as a driver's license. Thus, the image is assumed to accurately represent the proper patient in the system. The image of patient 502 is one that has been recently captured by the device (e.g., a slate or tablet computer) that provides the images, and is not yet assumed to represent the proper member of the healthcare organization. The image of patient 500 may have been obtained automatically by a system with which the computer is communicating by characterizing the face in the captured image and comparing it to data that characterizes faces in previously-captured images of properly identified patients, such as patient 500. Here, the image of patient was identified as a match, and it is presented on the display so that the user of the computer can manually confirm that it is the right patient.

Various EMR data may be retrieved for the patient 500 when such a determination is made. For example, the identified patient's name, age, gender, birthdate, and age are shown with the image of the patient 500, so as to help the user confirm the identification of the patient 500 as being the right match. Also, other data can be provided. As one example, vital sign data 504 is shown and may be populated as the information is collected from patient 502 (though only populated into the EMR after patient 502 is confirmed as being the same person as patient 500). Such collection may occur via manual data entry by the user of the computer and/or by wired or wireless connection between peripherals for collecting such data (e.g., a blood pressure cuff) and the computer.

Other data may be historical data that was collected earlier for the patient 500, and that provides a patient history for the user to review and perhaps update. For example, medications data 506 shows medications that the patient 500 is taking, allergies data 508 shows known allergies of the patient 500, immunization data 510 shows immunizations that the patient 500 has received and the dates of such immunizations, and problems data shows symptoms or diagnoses of prior problems for the patient. Each of the areas displaying EMR data may be expanded or collapsed as a user see fit, such as Health Maintenance area 514 which is collapsed and the other areas just discussed which are expanded, so that more data may be displayed for the patient 500 and displayed in a manner that data that is currently of interest to the user can be the focus of the user.

Figure 5B:
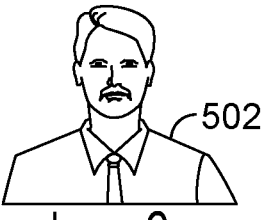

FIG. 5B shows a patient and guardian visual comparison display. For example, two images can be acquired at the current time when the patient is a minor or otherwise needs a guardian to act for the patient. Those images may be sent to a facial-recognition server system and compared to data for previously-captured and saved images. The display here may be shown when matches for the patient and the guardian are identified by the server system. In certain embodiments, the data for the recently-captured image of the guardian may be compared to all guardians or all users in the system, and then the previously stored image for the patient may be identified by correlating the guardian to the patient based on their relationship. Such use of the guardian's facial image to make the match may be preferable because the faces of minors may be expected to change more than the faces of adults, so that adults are more likely to provide a positive accurate match. In this example, image 520 shows a previously-stored image of the patient and image 522 shows a previously-stored image of the guardian, along with a message 524 indicating that the system has determined automatically that there is a match. The user of the device may look at these images and at the people standing in front of the user in order to perform a quick manual confirmation that the system got things right. If the system did not, the user may, for example, ask the guardian for a driver's license, passport, or other such manual identification, and may manually enter information from the identification in a normal manner, or may take a photo of the identification and have the system perform, for example, optical character recognition on the identification in order to produce text from the identification and to parse out the text that is relevant (e.g., first and last name, and address).

As discussed above, one example in which guardian faces may be checked is in newborn wards at a hospital. In particular, putative parents may be required to undergo a facial scan and match before they are given their newborn baby. Optionally, the face of the baby may be scanned to confirm that there is a double match. In certain situations, particular rules may be set for a particular newborn, such as allowing a mother to take the baby, but not the father.

In certain implementations, a flag may be set for users who are likely to have someone who is a facial match for them, so that a user of a system will be more careful in making a manual confirmation of a prospective patient's identity. For example, if a patient is an identical twin, a flag may be set for the patient, so that a health care provider is warned when a medical record is fetched for that user, so as to alert the provider that they may be treating one twin but looking at the records for the other twin. Similar flags may be set if a particular patient has checked in at a facility in the past, and a healthcare provider has indicated to the system that it has returned an inaccurate match (a false positive).

Figure 5D:
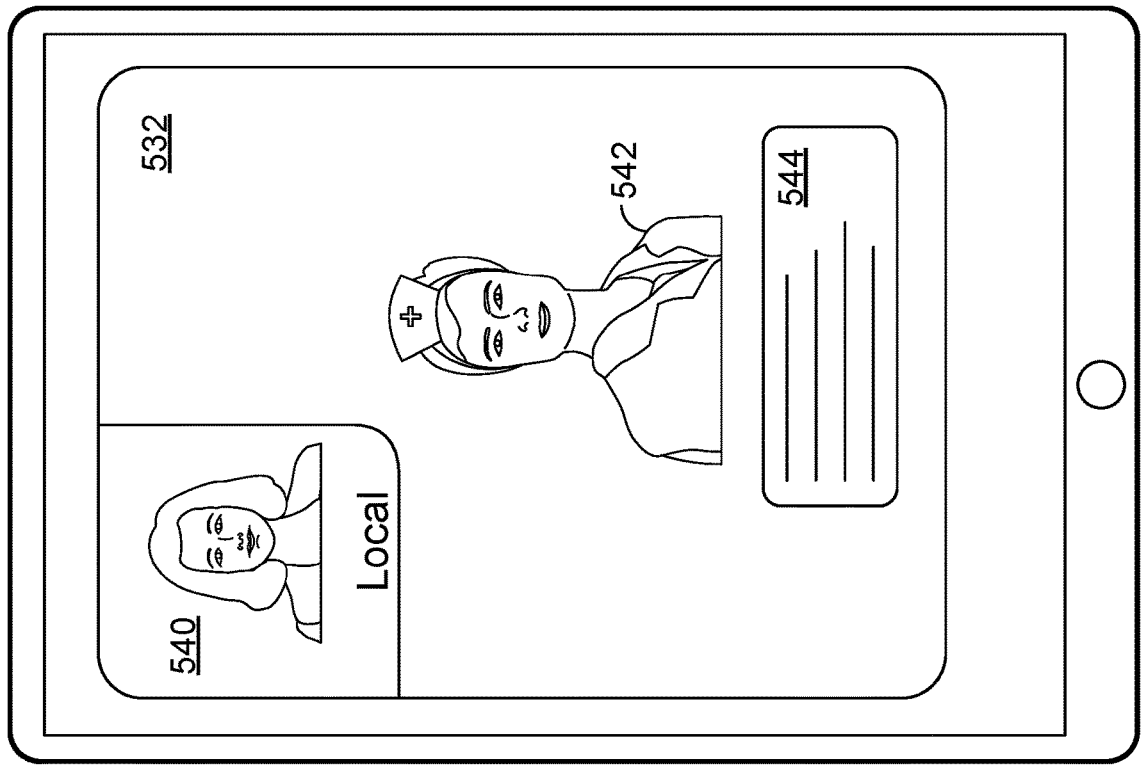
Figure 5C:
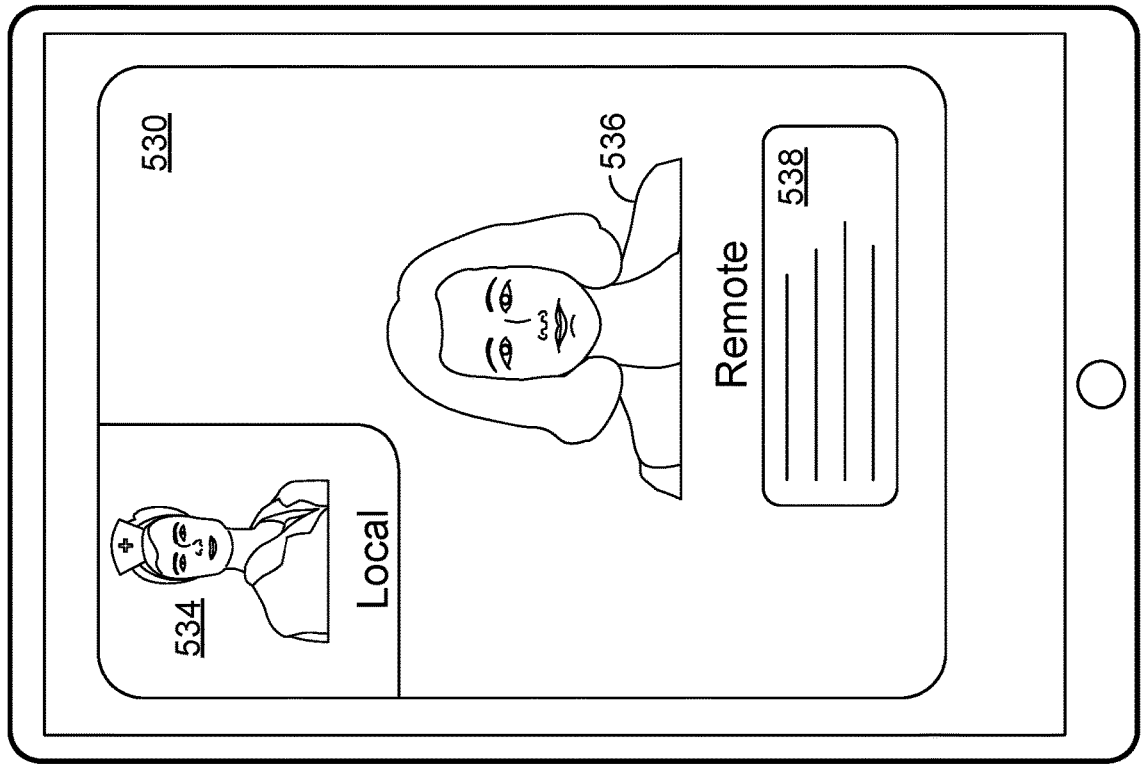

FIGS. 5C and 5D show respective displays for a nurse and a physician who are discussing a particular patient via video conference, which may occur over a wireless network (e.g., WiFi, 3G, or 4G) and the internet in known manners. The conference may be augmented by using a facial recognition system and a textual tracking application so as to document and verify the information that is shared in the conference. For example, display 530 shows a moving real-time image 534 of the person who is holding the device, here a nurse, and an image 536 of the person on the other end of the conversation. In the converse, display 532 shows the physician in image 540 and the nurse in image 542. The two participants can speak back-and-forth with each other in a familiar manner, and can also type instructions in a chat box 538, 544 in a familar manner. For example, the physician may type information for a mode of treatment for a patient, such as by typing the name of a drug to give the patient and also an amount and schedule for providing the drug.

When the conference starts, each device may capture and send an image of its respective user automatically to a central server system that is programmed for facial matching. Each device may store text that identifies its user (e.g., from when the user logged onto the device) and may send that text to the server system also. The server system may use the text to obtain data that characterizes an earlier-captured image of each of the users, and may compare that data to data from the just-captured images of the respective users. The system may subsequently capture and store textual information, and audio and/or video of the teleconference. Such information may be used to determine, at a later date, whether particular communications were made or instructions given, whether verbally or in a typed manner.

Figure 6:
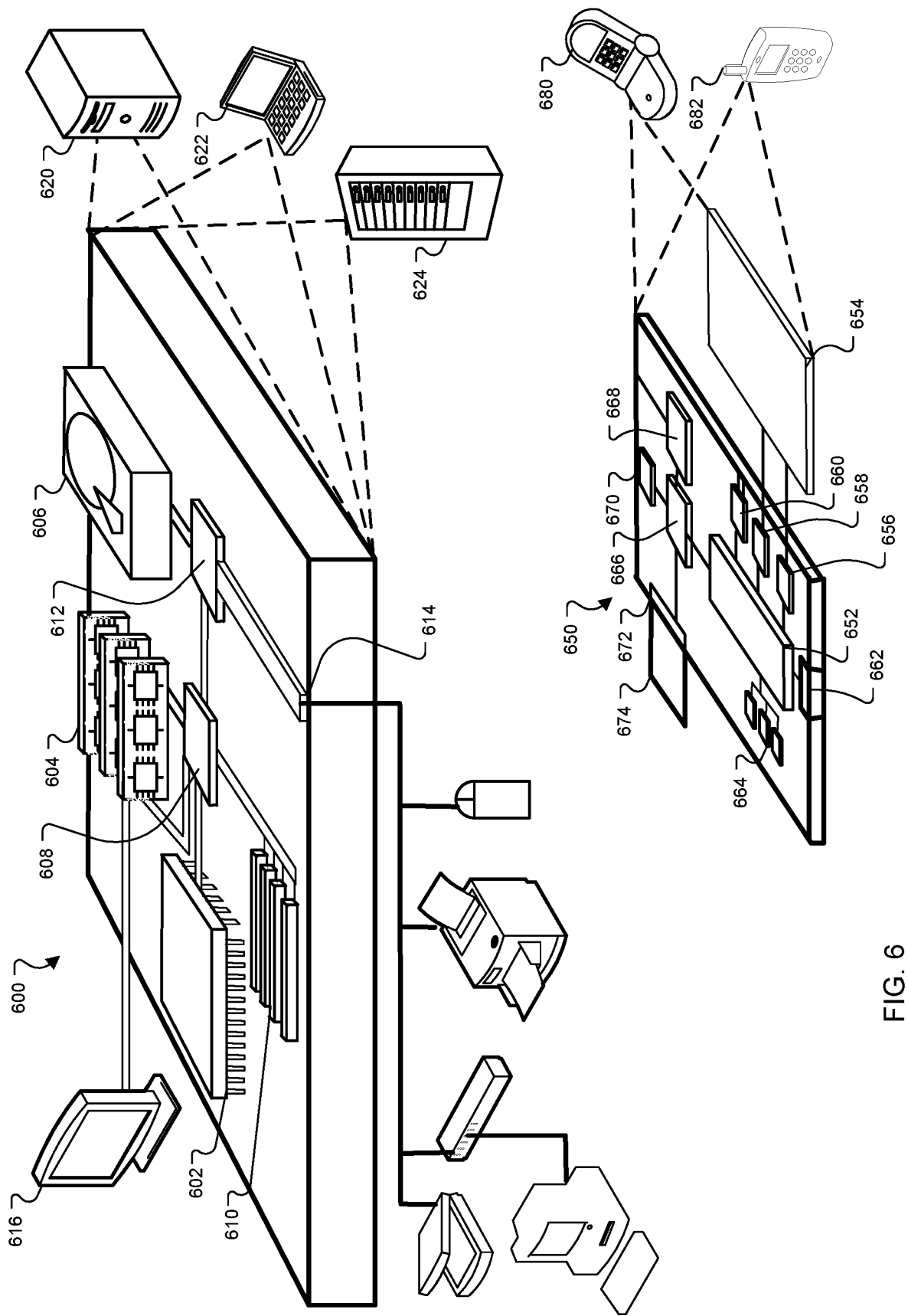
FIG. 6 shows schematic diagrams of a general computer system and a general mobile computing device that may implement the techniques described in this document.

FIG. 6 shows schematic diagrams of a general computer system 600 and a general mobile computing device 650 that may implement the techniques described in this document. Computing device 600 is intended to represent various forms of digital computers, such as laptops, desktops, workstations, personal digital assistants, servers, blade servers, mainframes, and other appropriate computers. Computing device 650 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 600 includes a processor 602, memory 604, a storage device 606, a high-speed interface 608 connecting to memory 604 and high-speed expansion ports 610, and a low speed interface 612 connecting to low speed bus 614 and storage device 606. Each of the components 602, 604, 606, 608, 610, and 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as display 616 coupled to high speed interface 608. In other implementations, multiple processors and/or multiple buses may be used, as appropriate, along with multiple memories and types of memory. Also, multiple computing devices 600 may be connected, with each device providing portions of the necessary operations (e.g., as a server bank, a group of blade servers, or a multi-processor system).

The memory 604 stores information within the computing device 600. In one implementation, the memory 604 is a volatile memory unit or units. In another implementation, the memory 604 is a non-volatile memory unit or units. The memory 604 may also be another form of computer-readable medium, such as a magnetic or optical disk.

The storage device 606 is capable of providing mass storage for the computing device 600. In one implementation, the storage device 606 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 604, the storage device 606, memory on processor 602, or a propagated signal.

The high speed controller 608 manages bandwidth-intensive operations for the computing device 600, while the low speed controller 612 manages lower bandwidth-intensive operations. Such allocation of functions is exemplary only. In one implementation, the high-speed controller 608 is coupled to memory 604, display 616 (e.g., through a graphics processor or accelerator), and to high-speed expansion ports 610, which may accept various expansion cards (not shown). In the implementation, low-speed controller 612 is coupled to storage device 606 and low-speed expansion port 614. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 620, or multiple times in a group of such servers. It may also be implemented as part of a rack server system 624. In addition, it may be implemented in a personal computer such as a laptop computer 622. Alternatively, components from computing device 600 may be combined with other components in a mobile device (not shown), such as device 650. Each of such devices may contain one or more of computing device 600, 650, and an entire system may be made up of multiple computing devices 600, 650 communicating with each other.

Computing device 650 includes a processor 652, memory 664, an input/output device such as a display 654, a communication interface 666, and a transceiver 668, among other components. The device 650 may also be provided with a storage device, such as a micro drive or other device, to provide additional storage. Each of the components 650, 652, 664, 654, 666, and 668, are interconnected using various buses, and several of the components may be mounted on a common motherboard or in other manners as appropriate.

The processor 652 can execute instructions within the computing device 650, including instructions stored in the memory 664. The processor may be implemented as a chipset of chips that include separate and multiple analog and digital processors. The processor may provide, for example, for coordination of the other components of the device 650, such as control of user interfaces, applications run by device 650, and wireless communication by device 650.

Processor 652 may communicate with a user through control interface 658 and display interface 656 coupled to a display 654. The display 654 may be, for example, a TFT LCD (Thin-Film-Transistor Liquid Crystal Display) or an OLED (Organic Light Emitting Diode) display, or other appropriate display technology. The display interface 656 may comprise appropriate circuitry for driving the display 654 to present graphical and other information to a user. The control interface 658 may receive commands from a user and convert them for submission to the processor 652. In addition, an external interface 662 may be provide in communication with processor 652, so as to enable near area communication of device 650 with other devices. External interface 662 may provide, for example, for wired communication in some implementations, or for wireless communication in other implementations, and multiple interfaces may also be used.

The memory 664 stores information within the computing device 650. The memory 664 can be implemented as one or more of a computer-readable medium or media, a volatile memory unit or units, or a non-volatile memory unit or units. Expansion memory 674 may also be provided and connected to device 650 through expansion interface 672, which may include, for example, a SIMM (Single In Line Memory Module) card interface. Such expansion memory 674 may provide extra storage space for device 650, or may also store applications or other information for device 650. Specifically, expansion memory 674 may include instructions to carry out or supplement the processes described above, and may include secure information also. Thus, for example, expansion memory 674 may be provide as a security module for device 650, and may be programmed with instructions that permit secure use of device 650. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 664, expansion memory 674, memory on processor 652, or a propagated signal that may be received, for example, over transceiver 668 or external interface 662.

Device 650 may communicate wirelessly through communication interface 666, which may include digital signal processing circuitry where necessary. Communication interface 666 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 668. In addition, short-range communication may occur, such as using a Bluetooth, WiFi, or other such transceiver (not shown). In addition, GPS (Global Positioning System) receiver module 670 may provide additional navigation- and location-related wireless data to device 650, which may be used as appropriate by applications running on device 650.

Device 650 may also communicate audibly using audio codec 660, which may receive spoken information from a user and convert it to usable digital information. Audio codec 660 may likewise generate audible sound for a user, such as through a speaker, e.g., in a handset of device 650. Such sound may include sound from voice telephone calls, may include recorded sound (e.g., voice messages, music files, etc.) and may also include sound generated by applications operating on device 650.

The computing device 650 may be implemented in a number of different forms, as shown in the figure. For example, it may be implemented as a cellular telephone 680. It may also be implemented as part of a smart phone 682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention. For example, much of this document has been described with respect to matching of prospective patients to pre-acquired image data for previously registered members of a healthcare system, but other forms of image qualification of people may be employed, including qualifying caregivers in certain ways (e.g., to establish a right to access certain items) or tracking caregiver actions, checking people who are acting on behalf of a patient, and other such activities.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A computer-implemented method for selectively providing access to medical record information, the method comprising:
    receiving, at a computer system of a healthcare provider, one or more digital images of a healthcare patient from a computing device that corresponds to a user account that is authorized to obtain information about patients in a healthcare system;
    converting data for the one or more digital images through a one-way electronic function such that the converted data cannot be used to reconstruct the one or more digital images;
    providing, to a facial recognition system of a third-party that is separate from the healthcare provider, the converted data that is generated from the one or more digital images of the healthcare patient;
    receiving, from the facial recognition system of the third-party, one or more identifiers that correspond, in a system of the healthcare provider, with one or more registered members of the healthcare system and to obtain a member identifier, the identifiers generated by matching the provided data to data corresponding to images previously captured of the one or more members of the healthcare system, wherein the one or more identifiers do not provide personally identifiable information for the patient outside the computer system of the healthcare provider;
    obtaining electronic medical record information about one of the one or more members based on determining that the healthcare patient is the one of the one or more members; and
    providing some or all of the obtained electronic medical record information to the computing device.

2. The computer-implemented method of claim 1, further comprising applying the one-way function to data for the one the one or more digital images of the healthcare patient before providing data to the third-party, to prevent the facial recognition system of the third-party from accessing the one or more digital images of the healthcare patient.

3. The computer-implemented method of claim 2, wherein the computer system of the healthcare provider and the facial recognition system of the third party pass data through defined application programing interfaces (APIs).

4. The computer-implemented method of claim 1, further comprising identifying the patient with a first captured image at a check-in to a medical facility and subsequently identifying the patient with a second captured image at a location in the facility of a procedure to be performed on the patient or a medication being provided to the patient.

5. The computer-implemented method of claim 1, further comprising displaying one of the one or more digital images at a point-of-care for the patient, to allow a caregiver to visually verify that a person about to receive care from the caregiver is the patient.

6. The computer-implemented method of claim 1, further comprising generating billing information for care provided to the patient based on the identification of the patient from the facial recognition.

7. The computer-implemented method of claim 1, further comprising identifying the patient using a combination of (a) data from the one or more digital images, and (b) meta data that describes the patient.

8. The computer-implemented method of claim 7, wherein the data from the one or more digital images generates an ambiguous result, and the meta data is used to disambiguate the ambiguous result.

9. The computer-implemented method of claim 1, wherein the patient is a minor, and additional digital images are used to match parents for the minor to the minor.

10. The computer-implemented method of claim 1, further comprising using identification of the patient to determine that the patient has made an excess number of check-ins with the healthcare system.

11. The computer-implemented method of claim 1, further comprising displaying the one or more digital images to a caregiver along with one or more previously-captured images so as to allow the caregiver to confirm that the patient matches a patient of record.

12. The computer-implemented method of claim 1, further comprising capturing a digital image of a caregiver and providing access to medical records for the patient by the caregiver only if the caregiver matches an approved caregiver.

13. The computer-implemented method of claim 1, further comprising generating a diagnosis for the healthcare patient from the one or more digital images.

* * * * *